United States Patent [19]

Marquardt

[11] Patent Number: 5,042,487
[45] Date of Patent: Aug. 27, 1991

[54] EXAMINATION UNIT INCLUDING POSITIONABLE PATIENT CHAIR, EXAMINATION DEVICE AND SUPPORT SYSTEM

[76] Inventor: Mark R. Marquardt, 925 Monticello Dr., Naperville, Ill. 60540

[21] Appl. No.: 435,562

[22] Filed: Nov. 13, 1989

[51] Int. Cl.⁵ .............................................. A61B 5/05
[52] U.S. Cl. ..................... 128/653 A; 128/653 SC; 128/377; 269/325; 378/17; 378/196
[58] Field of Search ...... 128/653 A, 653 AF, 653 SC, 128/653 S, 376, 377; 269/323, 328; 378/11, 17, 20, 195–197

[56] References Cited

U.S. PATENT DOCUMENTS

| | | |
|---|---|---|
| 2,244,778 | 6/1941 | Harsley ................................. 378/197 |
| 2,281,931 | 5/1942 | Frank . |
| 3,432,660 | 3/1969 | Anger . |
| 3,504,179 | 3/1970 | Hainault ............................... 378/195 |
| 3,670,163 | 6/1972 | Lajus .................................... 378/196 |
| 3,766,387 | 10/1973 | Heffan et al. . |
| 3,922,552 | 11/1975 | Ledley .................................. 378/17 |
| 4,112,393 | 3/1978 | Brandt . |
| 4,115,695 | 9/1978 | Kelman ................................ 378/17 |
| 4,316,091 | 2/1982 | Bernardi . |
| 4,472,822 | 9/1984 | Swift . |
| 4,669,103 | 5/1987 | Barnea .................................. 378/11 |
| 4,691,332 | 9/1987 | Burstein et al. . |
| 4,719,425 | 1/1988 | Ettinger ............................. 128/653 A |
| 4,875,485 | 10/1989 | Matsutani ......................... 128/653 SC |

Primary Examiner—Stephen C. Pellegrino
Assistant Examiner—Robin R. Longo
Attorney, Agent, or Firm—Hill, Van Santen, Steadman & Simpson

[57] ABSTRACT

An apparatus and method is disclosed for medically examining a patient's spine using a non-invasive technique such as computerized tomography (CT). In this apparatus and method the patient is seated in a generally vertically-oriented chair which is tiltable in a forward and rearward direction, is pivotable relative to a vertical axis, is vertically movable and is stationary so as to adjustably induce gravitational effects on the patient's back. A pivotable chair back can be included for controllably applying additional loads or flexion to the patient's back. An annularly-shaped examination device, such as as CT device, is horitonzally positioned on a support frame over the patient who is aligned with a central opening in the device. The device can be positioned about the patient and oriented horizontally or angularly displaced relative to the horizontal for optimizing or adjusting the generated image. The examination device may be tiltable about a horizontal axis transverse to the direction of tilting of the chair. Appropriate mechanisms are provided for the previously-described adjustment.

1 Claim, 3 Drawing Sheets

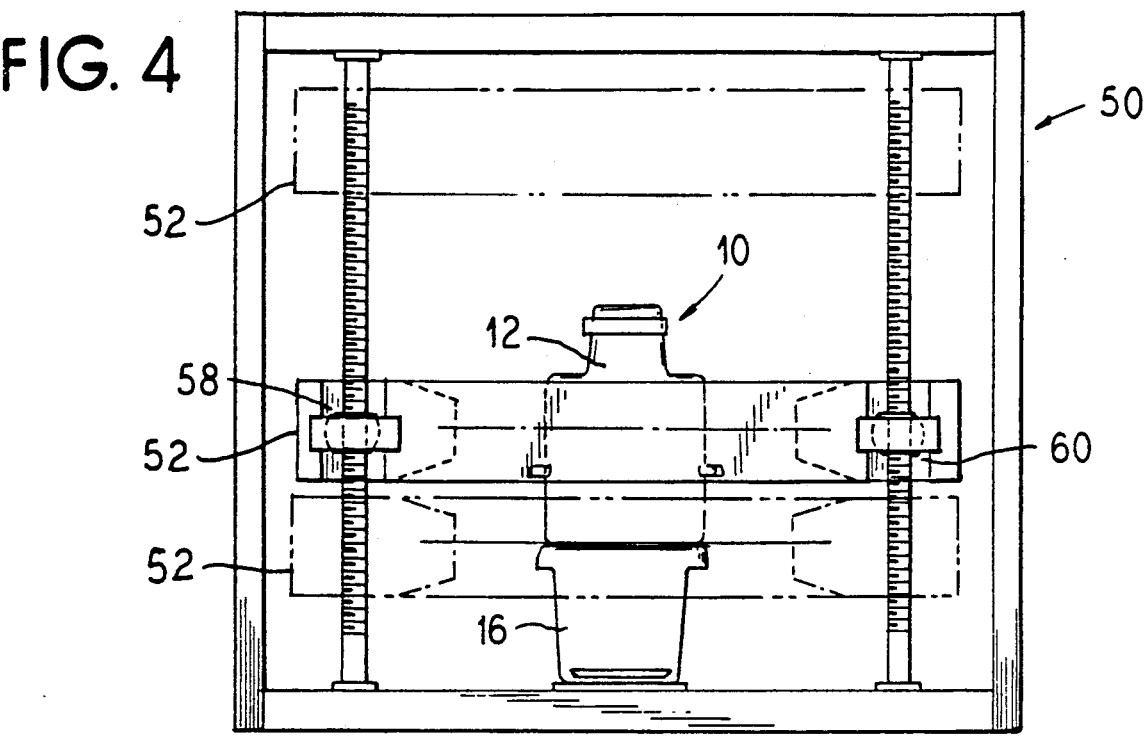
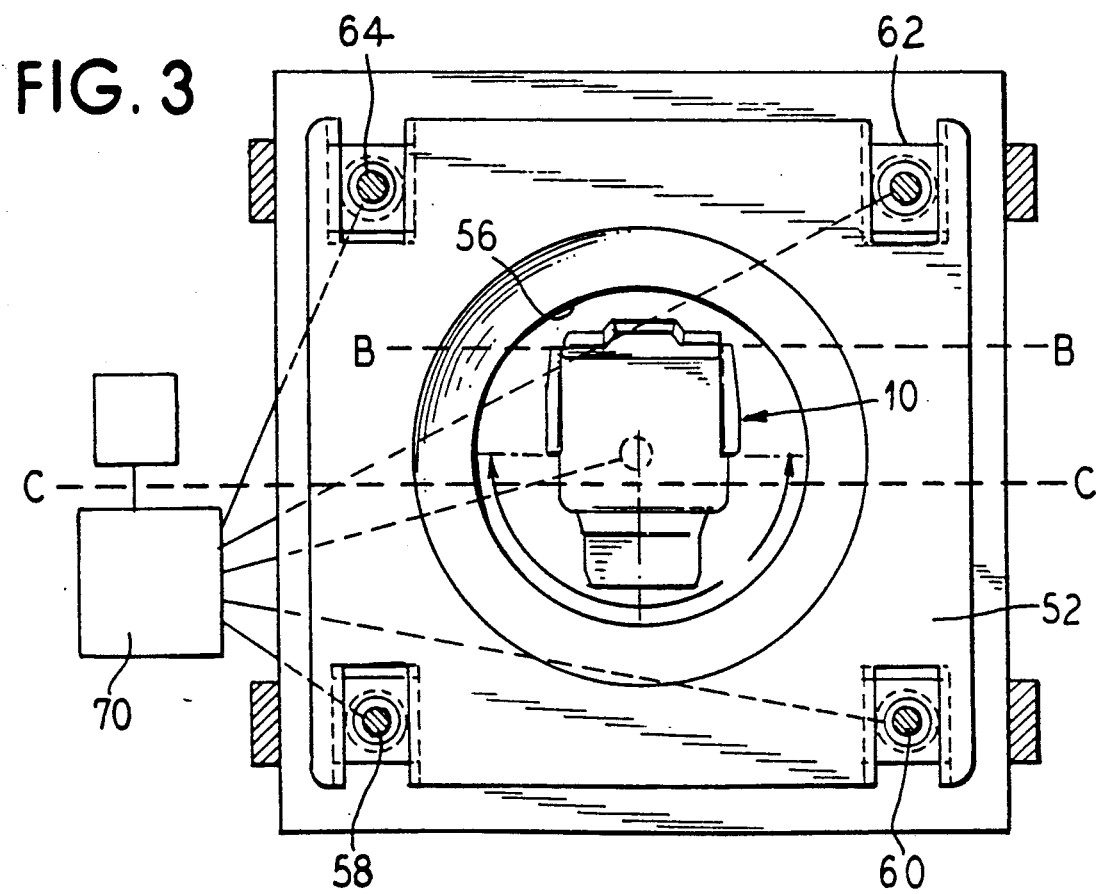

EXAMINATION UNIT INCLUDING POSITIONABLE PATIENT CHAIR, EXAMINATION DEVICE AND SUPPORT SYSTEM

BACKGROUND OF THE INVENTION

This invention relates to medical diagnosis, and more particularly, to an apparatus and process for examination and diagnosis of spinal disorders such as intervertebral disc herniations.

Numerous non-invasive diagnostic or non-destructive testing or imaging techniques are known. The techniques include radiation techniques, such as X-ray, gamma-ray, and computerized tomography (CT) and magnetic resonance imaging (MRI) techniques. Such techniques have been used in both industrial and medical examination.

Examples of such systems and techniques are seen in U.S. Pat. Nos. 4,691,332; 4,472,822; 4,316,091; 4,112,303; 3,766,387; 3,432,660; and 2,281,931.

Medical examination devices are generally annularly- or ring-shaped and vertically oriented and the patient is examined in the central opening along a horizontal axis that is generally normal or perpendicular to the device. Most frequently due to considerations relating to the weight of the examination device and patient comfort, patients are examined in a horizontal or supine position.

However, various of the foregoing techniques have been used to examine standing patients and seated patients for dental and brain-related purposes. Moreover, some devices are said to be capable of examining patients in a vertical position but are believed to pose stability problems, etc.

A great percentage of the population has back problems which necessitates examination and diagnosis of the spine. Moreover, it is known that stress on the back or spine is minimized in a lying or supine position, and it is also known that stress may be induced in upright seated positions due to the effects of gravity on the spine. Furthermore, it is known that flexion of the spine while seated will additionally increase the load and stress in the spine and increase the pressure within the intervertebral disc, causing it to bulge if damaged.

Currently, examination is done with the patient in the horizontal position so as to minimize discomfort and maximize the convenience in use of present equipment. However, in order to examine the back, it is believed that the patient should be subjected to stresses he may normally encounter (such as from gravity) and that during examination it may be desirable to variably and controllably stress the patient's back.

It is the object of this invention to provide an apparatus and method for examination of patients with a back-related problem in which the effects of gravity can be induced and the stress conditions can be variably and controllably applied.

These and other objects of this invention will become apparent from the following disclosure and appended claims.

SUMMARY OF THE INVENTION

There is disclosed herein an apparatus and process for examining a patient in a generally upright position wherein gravity-related stress on the spine can be induced and stress can be variably and controllably applied. With the present invention such stresses can be controllably applied to a patient and the patient may be examined by computerized tomography. In practice the patient is seated in an adjustable chair that tilts or rocks in a forward and a rearward direction, moves vertically, is pivotable about a vertical axis so as to orient the patient to induce the stress effects of gravity. The chair back is pivotable so as to permit selective additions of load to the back. The patient may be in a substantially upright orientation.

The diagnostic imaging or CT device is a large, heavy and ring- or annularly-shaped device. The device is supported and oriented in a generally horizontal plane above the patient's chair so that a vertical axis substantially along a patient's spine passes through the central opening of the unit. The device can be moved vertically upwardly or downwardly along the vertical axis so as to surround the patient and permit examination in a series of horizontal planes.

An appropriate support mechanism is provided for safely and adjustably supporting the device above and about the patient. In this system the examination device is supported on three or four points for stability. Moreover, the device is tiltable relative to a horizontal axis to provide more flexibility in examination.

This technique is believed to provide accurate data as to the condition of the spine under stress and minimize erroneous data and inaccurate diagnosis as may have resulted from prior techniques. Moreover, it is to be noted that in this system the patient is stationary during examination, and thus motion sickness such as vertigo is avoided.

BRIEF DESCRIPTION OF THE DRAWINGS

FIG. 3 is a plan view of an annularly-shaped diagnostic imaging device supported in the horizontal plane by four corner supports with a patient's chair vertically oriented with respect to the central opening thereof;

FIG. 4 is a front elevational view showing the examination device positioned above the patient's examination chair with the examination device shown in dotted lines in a lower position and with the chair having a patient restraint system;

DESCRIPTION OF THE PREFERRED EMBODIMENT

Figure 1:
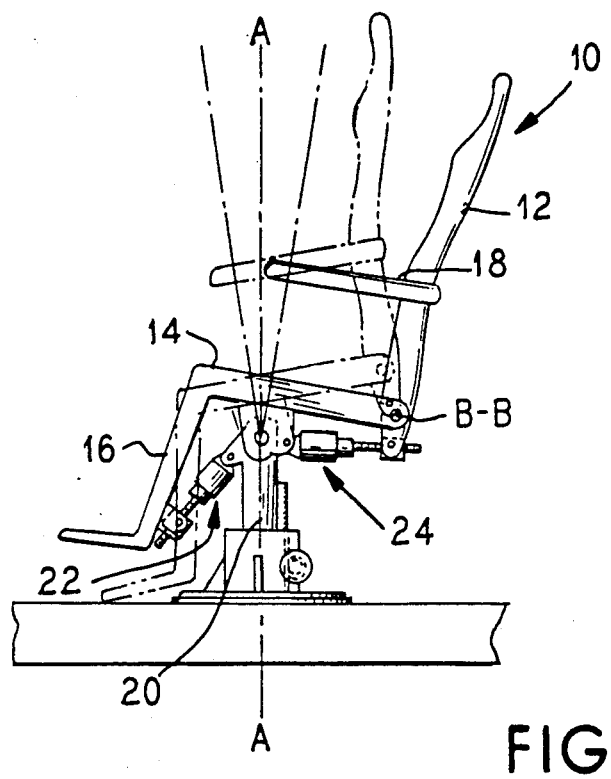
FIG. 1 is an elevational view of a patient's chair showing the tiltable positioning thereof.
Figure 2:
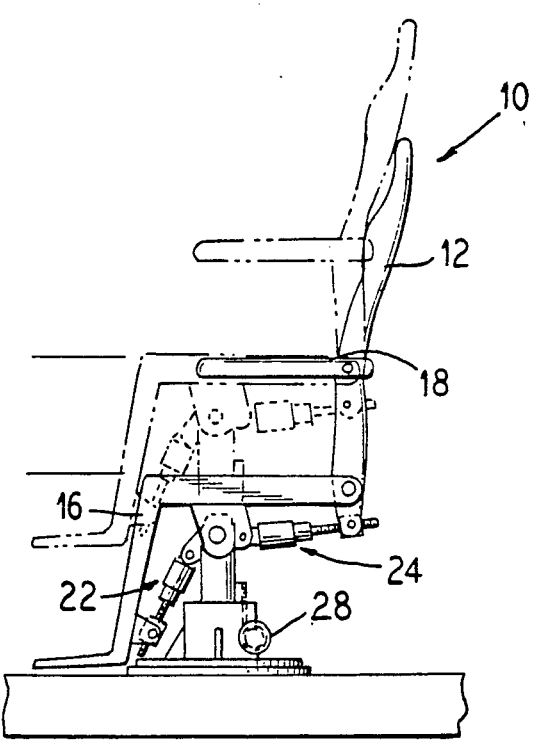
FIG. 2 is an elevational view of a patient's chair as in FIG. 1 showing vertical movement thereof.

The complete examination unit and process includes concepts related to and the interrelationship between the patient's support chair, the examination device, support system, adjustment features and the resultant image. These elements cooperate in combination but for convenience of discussion are considered separately hereinafter.

The Chair

The chair 10 upon which a patient is seated includes a pivotable back 12, a seat portion 14, leg support portions 16, and an arm rest such as 18. An appropriate central support 20 can be provided.

A centrally-positioned vertical axis A—A is shown extending upwardly through the seat and can be generally parallel to the chair back and a patient's spine, in the normal or vertical position.

The chair is controllably tiltable or rockable in the forward and rearward direction. The limits of tilting are determined by practical considerations such as stability, interference with the examination device, etc. This tilting movement can be achieved by commonly available motor drive systems and control of tilting is by an operator using a control system.

A typical motor drive system may include jack screw arrangements, such as 22, which is secured to the central support and the leg. By expansion or retraction of the jack screw, tilting of the chair can be achieved.

The chair back 12 can be pivoted or flexed about a pivot axis B—B at the back of the seat where the seat and back join each other. The flexing of the back is in the front and back direction and can be in the range of ±45°.

The limits of flexing are determined by the practical considerations such as the flexibility of the patient's spine. Movement of the chair back is by conventional means and can be controlled by the operator. The jack screw 24 is secured to the central support and back.

Figure 6:
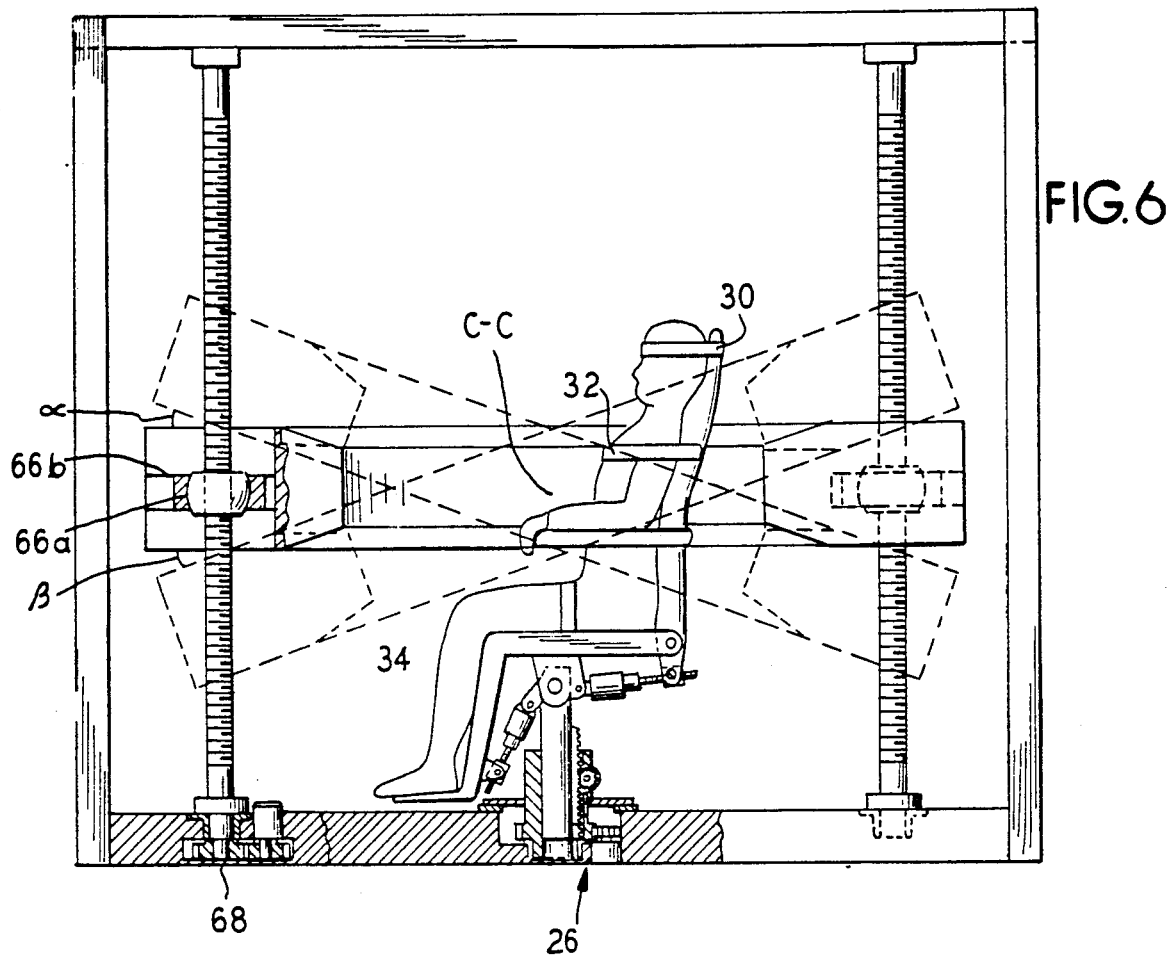
FIG. 6 is a side elevational view showing the examination device in an intermediate position and suggesting tiltable movement thereof along a horizontal axis.

Moreover, the chair can be pivoted about the vertical axis to the left or right in amount of about ±90°. This is best seen in FIG. 3. This rotation permits ease of entry and, if necessary, patient positioning. This also can be controlled by the operator. A drive and gearing mechanism 26 of a standard type is shown in FIG. 6 for rotating the chair.

The tilting, rotation and flexion ability permits the orientation of a patient at positions where the patient's angular relation to an examining device can be changed, stress controllably induced, and the spine imaged.

In addition, the chair 10 can be controllably moved vertically approximately 350 mm. This also for the purposes of examination and alignment. This vertical movement is to permit the patient to be incrementally moved upwardly through the device so as to permit examination of selected sections of the patient.

Only one section of a patient is examined at a time, but the patient can be moved incrementally with respect to the unit so as to obtain the multiple views. In this situation the chair is vertically movable about 350 mm, and therefore a section of the patient about 350 mm long can be examined using multiple views. To achieve this vertical movement, a rack and pinion system 28 as shown in FIGS. 1 and 6 can be used.

Patient restraints such as a head restraint 30, body restraint 32 and lap restraint 34 can be used. These are to cooperate in holding the patient in a stationary position so as to optimize image clarity. Each of the restraints may be a pair of straps that are fastened to the chair and are secured together at their ends by a hook-and-loop or Velcro-type fastener.

With this arrangement the patient can be moved vertically, tilted, or rotated separately or simultaneously and the patient's back flexed so as to adjust the stress on the patient and his attitude relative to the examination or diagnostic device so as to optimize examination and imaging.

The total effect of this movement is to permit a high degree of freedom in positioning and stressing the patient for examination.

The Examination Device

The examination device 50 generally includes the diagnostic imaging device 52, such as a CT scanner, that is mounted in a supporting frame or gantry 54 for vertical movement with respect to the examination chair 10 generally.

The examination device 52 is generally annular, is generally horizontally oriented, and has a large central opening 56. The device 52 is mounted in the frame 54 for orientation in a substantially horizontal plane and movement in a vertical direction. Some up-and-down tilting or angular displacement from the horizontal orientation is permitted about an axis such as C—C, which is horizontal and transverse to the direction or plane of tilting for the chair.

Figure 5:
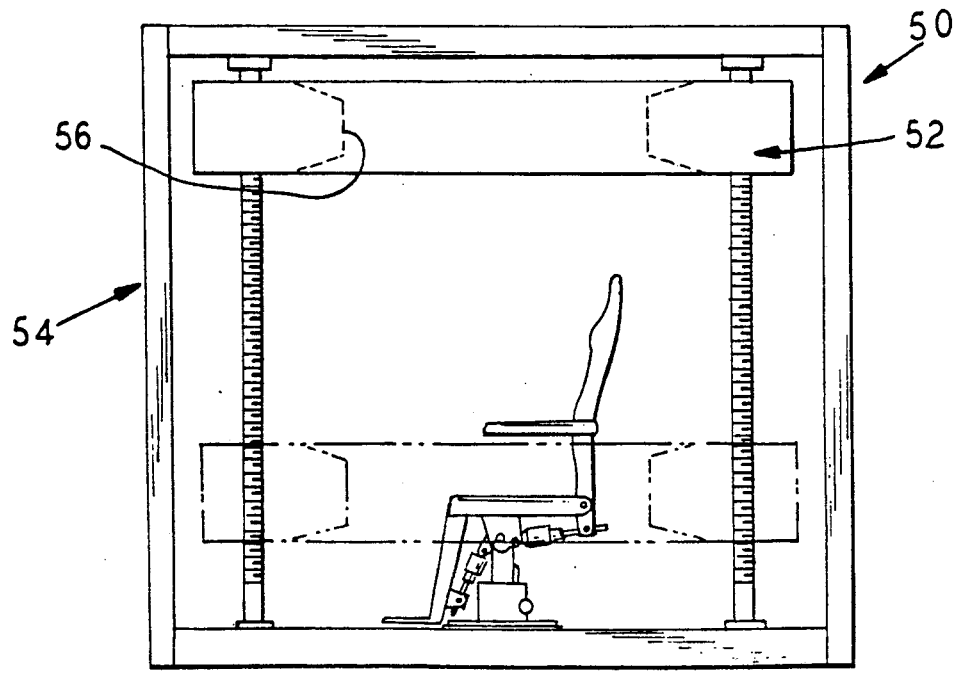
FIG. 5 is a side elevational view similar to FIG. 4 showing the examination device, the patient's chair and the movement of the chair back.

The patient, chair, and examination device are mounted with respect to one another, such that the device can be moved by an operator generally parallel to the patient and the chair's vertical axis and can be moved to surround the patient chair. This positioning is best seen in FIGS. 4 and 5 where the device 52 has been lowered from an upper position to a lower examining position surrounding the chair 10 and patient. The travel of the examination device or the distance between the uppermost and lowermost positions is about 1860 mm. This is a convenient distance based on the probable height of an examining room ceiling and for entry of a patient into the examination device.

Figure 7:
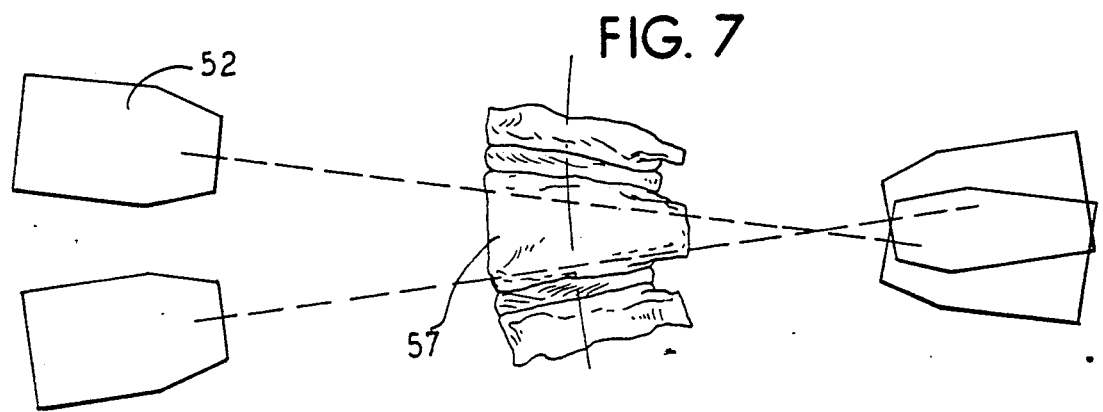
FIG. 7 is a diagrammatic view showing the nature of examination of a single disc by this system.

In addition, the examination device can be tilted by the operator about the horizontal plane or axis such as C—C. This tilting is desirable to permit adjustment of the device relative to the patient to enhance imaging. This is particularly true for the examination of a disc where the spine is curved, and it is desirable to view the disc in sections which are generally perpendicular to the disc axis. This type of positioning can also be referred to as angular displacement from the horizontal. FIG. 7 diagrammatically shows the selective positioning of an examination device relative to a disc such as 57.

Referring to FIG. 6, the examination device 52 is shown at an intermediate height at an angle of about 20°, or alpha $\alpha$, upwardly from the horizontal. The device can also be tilted downwardly at an angle of about 20° or $\beta$. As a practical matter, the angles $\alpha$ and $\beta$ are equal. The maximum tilt from the horizontal for examination purposes is based on practical construction details and may be about 20°. In other words $\alpha$ can be up to about 20° and $\beta$ can be up to about 20°. Tilting of the examination device can be under the operator's control.

The ability to selectively position the patient's chair and the ability to selectively position the examination device gives the examination personnel the ability to optimize the positioning of the patient and the device for stress and for examination and imaging.

The Support System

Operation of the device may result in the device having a tendency to wobble. Therefore, a minimum number of supports is three, and in the preferred embodiment, there are four pole-like supports 58, 60, 62 and 64.

The mechanism for moving the device up and down or tilting the same may be by a lead screw system in which movement of the device is based on movement along lead screws and parts and rotation of the screws. Universal joints are provided to permit tilting.

As previously indicated, the frame 54 and device 52 cooperate to support, move and tilt the device. The support poles 58, 60, 62 and 64 are threaded but controlled for rotation. The medical device includes a pivotable and lost motion connector assembly, such as 66, at each corner for connection and cooperation with each of the support poles. A typical connection includes a nut-like connection 66a, which is internally threaded and has an arcuate exterior bearing surface. The nut threads engage the pole threads for vertical movement of the device. The nut is mounted to the examination device in a slidable bearing block, such as 66b, which acts as the connector and a lost motion connection to accommodate the tilting of the device.

Appropriate motors, such as 68, are provided for raising, lowering and tilting the examination device. The controls, such as 70, control the entire system.

Operation

In this system, the patient's chair 10 is fixed or stationary during examination and thus avoids patient problems relating to rotation such as motion sickness, dizziness, vertigo, etc. However, the chair may be rotatable ±90°. to facilitate patient entry or exit from the device.

The device is annularly shaped and can include a radiation system such as X-rays which are emitted from a sender on one side of the device, pass through the patient, and are received on the other side of the device. The emitter and receiver are, in effect, rotated about the device and a computer assembles the received signals to form a horizontal view or image of the patient.

Examination of a series of successive horizontal images can locate or indicate the presence of problem areas. In order to obtain an optimized image, the positioning and tilting of the device is achieved and then the chair is operated to tilt, raise or rotate the same or increase the pressure on the back.

The patient is seated in the chair. Torso, lap, and head restraints are fastened. Arm rests are raised, lowered or removed as necessary, and the patient's arms are then secured away from the examination field if possible. The footrest is adjusted up, down or removed, whichever is found to maximize the mechanical stresses to the pelvis and spine. The seatback is then flexed or extended in order to appropriately stress the intervertebral disc ligaments and related connective tissues. Further flexion or extension of the seatback may be provided during examination in order to obtain comparative stress/load findings. The examination device on the gantry is then lowered over the patient to the field of examination. Should the operator deem it necessary, the examination device may be tilted. The operator may then sequentially scan at different examination levels by vertically displacing the chair or the gantry, whichever produces the desired level of control. Data acquisition and interpretation will then be made according to predetermined standards.

Operation of the examination device is by an operator who can view the image generated. Adjustment of the device or patient may be for the purpose of imaging a particular part of the spine or enhancing the image. Generally after the patient is seated, the control system 70 is operated to bring the imaging device into the proper range (i.e., in the sense of a coarse adjustment). Then the patient's chair is adjusted as to height tilt, pivot and back flexion to achieve a fine tuning. Thereafter, the device may be tilted or further chair adjustment made again using the control system 70. Once the desired image is captured, then a new image may be generated by the unit being incrementally moved or adjusted.

Although the invention has been described with respect to preferred embodiments, it is not to be so limited as changes and modifications can be made which are within the full intended scope of the invention as defined by the appended claims.

I claim as my invention:

1. A system for medical examination of a patient's spine under variable and controllable stress conditions which include inducement of gravitational effects, said system comprising:

chair means that is generally vertically oriented for adjustably positioning a seated patient, said chair means including means defining a seat for supporting a patient and a back movably positioned relative to said seat for engaging a patient's back, and stressing the back by tilting in the forward or reverse direction, and means for moving said chair means with respect to the vertical and for adjustably positioning the chair back relative to the chair seat;

examination means including an annularly-shaped CT-type examination device oriented in a generally horizontal attitude and having a central opening, said examination means for use in the internal examination of a patient in said chair means under stress condition;

support means which includes at least three vertically oriented pole-like members for engaging and supporting said examination means in said generally horizontal attitude and for moving said device upwardly and downwardly relative to the vertical and in surrounding relationship to said chair means in said examining position;

control means associated with said examination means and chair means for adjustably positioning each of said means;

imaging means associated with said examination means for imaging a patient's spine, which patient is seated on the chair means within said examination means; and said chair means being positioned within said support means and relative to said examination means so that said examination means may be moved downwardly around said chair means so as to surround the same for examination of the patient, whereby images of said patient in a generally vertical and stressed condition can be obtained.

* * * * *